United States Patent
Bouteyre et al.

(10) Patent No.: US 9,562,870 B2
(45) Date of Patent: Feb. 7, 2017

(54) METHOD AND DEVICE FOR NON-DESTRUCTIVE TESTING OF WIND TURBINE BLADES

(75) Inventors: Jacques Bouteyre, St Medard en Jalles (FR); Pascal Jouan, St Medard en Jalles (FR)

(73) Assignee: ASTRIUM SAS, Suresnes (FR)

(*) Notice: Subject to any disclaimer, the term of this patent is extended or adjusted under 35 U.S.C. 154(b) by 720 days.

(21) Appl. No.: 13/823,645

(22) PCT Filed: Sep. 27, 2011

(86) PCT No.: PCT/EP2011/066762
§ 371 (c)(1),
(2), (4) Date: May 23, 2013

(87) PCT Pub. No.: WO2012/041848
PCT Pub. Date: Apr. 5, 2012

(65) Prior Publication Data
US 2013/0235897 A1    Sep. 12, 2013

(30) Foreign Application Priority Data

Sep. 28, 2010 (FR) ..................... 10 57827

(51) Int. Cl.
*G01N 25/72* (2006.01)
*F03D 1/06* (2006.01)
*G01M 99/00* (2011.01)

(52) U.S. Cl.
CPC ............... *G01N 25/72* (2013.01); *F03D 1/065* (2013.01); *G01M 99/002* (2013.01); *F05B 2260/83* (2013.01); *Y02E 10/721* (2013.01)

(58) Field of Classification Search
CPC ............................ G01N 25/72; F03D 11/0091
See application file for complete search history.

(56) References Cited

U.S. PATENT DOCUMENTS 4,902,139 A * 2/1990 Adiutori ............... G01N 25/18
                                                    374/137
5,930,990 A * 8/1999 Zachary ................ F01K 21/047
                                                    60/39.091
(Continued)

FOREIGN PATENT DOCUMENTS

DE    197 20 461    2/1998
EP    2 218 912     8/2010
(Continued)

OTHER PUBLICATIONS

Paynter R J H et al: The use of a second harmonic correlation to detect damage in composite structures using thermoelastic stress measurements II, Strain, vol. 39, No. 2, May 21, 2003 (May 21, 2003), pp. 73-78, XP002636455, British Soc. Strain Meas. UK ISSN.

(Continued)

Primary Examiner — Paul West
(74) Attorney, Agent, or Firm — Young & Thompson

(57) ABSTRACT

The method CND of non-destructive testing of a wind turbine blade includes: stressing the structure of the blade through a modification of a physical characteristic of a fluid filling the hollow interior volume of the blade; observing zones to be tested of the exterior surface of the blade, with the contactless measurement of a physical parameter on points of the exterior surface of the blade; and comparing the map of the values of the physical parameter measured with a reference map. A corresponding system CND for checking the structural integrity of a wind turbine blade includes an aerothermic device for modifying the physical conditions, temperature or pressure, of a fluid filling the hollow interior volume of the blade, a device for contactless measurement of a physical parameter, temperature or dimensions, of the (Continued)

Figure 1:
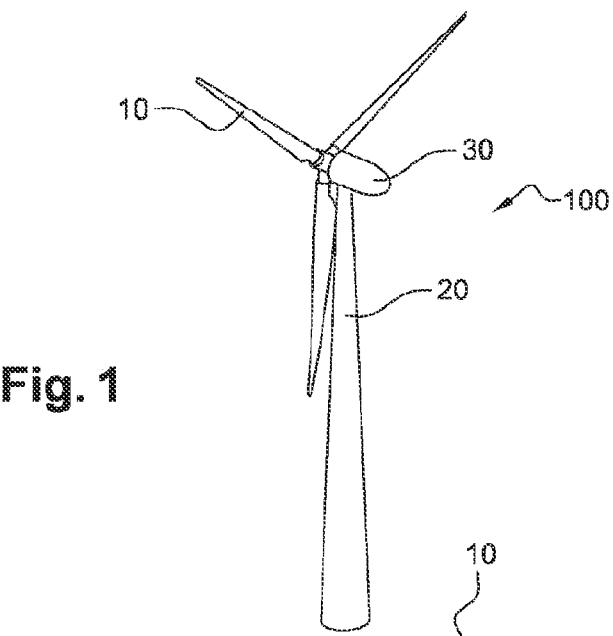

exterior surface of the blade, and a device for processing the measurements.

14 Claims, 4 Drawing Sheets

(56) References Cited

U.S. PATENT DOCUMENTS

| | | | |
|---|---|---|---|
| 8,197,129 | B2 | 6/2012 | Goldammer et al. |
| 2003/0101798 | A1 | 6/2003 | Kendall |
| 2006/0018752 | A1* | 1/2006 | LeMieux .................. F01D 11/00 416/96 R |
| 2010/0208247 | A1 | 8/2010 | Bosselmann et al. |

FOREIGN PATENT DOCUMENTS

| | | |
|---|---|---|
| WO | 03/069324 | 8/2003 |
| WO | 2008/031774 | 3/2008 |
| WO | 2008/119350 | 10/2008 |

OTHER PUBLICATIONS

Chatzakos P et al: "Autonomous Infrared (IR) thermography based inspection of glass reinforced plastic (GRP) wind turbine blades (WTBs)", IEEE Conference on Robotics, Automation and Mechatronics, RAM 2010, Jun. 28, 2010 (Jun. 28, 2010)-Jun. 30, 2010 (Jun. 30, 2010), pp. 557-562, XP002636453, IEEE Piscataway, NJ, USA DOI: 10.1109/RAMECH.2010.5513132.

Malinowski P et al: "Laser vibrometry for guided wave propagation phenomena visualisation and damage detection", AIP Conference Proceedings, vol. 1253, No. 1,May 28, 2010 (May 28, 2010) , pp. 140-149, XP002636454, 9th International Conference on Vibration Measurements by Laser and Non-Contact Techniques and Short Course, American Institute of Physics USA ISSN: 0094-243X.

Jensen F M et al: "Structural testing and numerical simulation of a 34m composite wind turbine blade", Composite Structures, vol. 76, No. 1-2, Oct. 1, 2006 (Oct. 1, 2006), pp. 52-61, XP025150595, Elsevier Science Ltd, GB ISSN: 0263-8223, 001: 10.1016/J. COMPSTRUCT.2006.06.008 [retrieved on Oct. 1, 2006].

* cited by examiner

METHOD AND DEVICE FOR NON-DESTRUCTIVE TESTING OF WIND TURBINE BLADES

The present invention belongs to the field of wind turbines.

More particularly, the invention relates to the non destructive testing of wind turbines blades integrity, more particularly, of large-sized wind turbines, that must be checked as much as possible without requiring to dismount the blades.

The field of the energy generation, in particular, of electric power, by the means of wind turbines is in fast growth. The economies seeking at a great scale and the interest to collect the maximum of energy per wind turbine lead to the design of increasingly large machines with blades of great lengths according to the span and posts carrying the nacelles of great heights.

The wind turbine blades currently reach in span dimensions higher than 50 m and prototypes of more than 75 m are in construction. These blades are the object of many constraints which result in producing these blades with metallic materials and/or composite materials.

The implemented composite materials are of the type including organic fibers such as Kevlar® fibers or mineral such as carbon or glass fibers which are kept into a matrix made of a hard organic resin in underlying layers, in order to form the various assembled elements of the blades.

Various known technologies can be implemented to manufacture such blades, but when the blade is in use on a wind turbine it undergoes strong mechanical constraints which require to carry out regular checks to make sure of its integrity and its good ageing.

The blades dimensions of large wind turbines do not allow, for economic considerations, to envisage the dismounting or transport of the blade to carry out frequent checks and those have thus to be realized on the wind turbine itself when the weather conditions allow it.

The quality of checks and their frequencies are then essential to detect the presence of defects, such as cracks, unstickings or delaminations, at the earliest steps of their occurrence and to repair the blades before a damage of the structure may impose significant repairs, or even put the integrity of the blade and the wind turbine in danger.

To carry out the checking of the blade structure the various known non destructive testing (NDT) techniques applied to the metallic structures or made from composite materials are usable on a wind turbine blade, in particular, the visual checking of the blade surface associated or not with sweating and fluorescence techniques, the checking of material and assemblies by radiography or ultrasounds. Such techniques are in particular implemented in factory to check the blades during their manufacture and before their assembly.

Whatever the NDT method implemented, a difficulty which arises in the case of the blades of wind turbine in service is due to difficulties encountered to reach all the points of the blade external surface in order to carry out the checking operations thereon.

Various solutions were imagined to solve the problem of the access to the various locations on the blades.

A known solution, for example, of documents WO2009/121792 and WO 2009/155918, consists in using a platform movable along the post that supports the wind turbine so that when a blade is maintained vertically downwards and thus in parallel to the carrying post, each points of the blade surface can be inspected at all the heights along the blade by operators working on the platform to carry out visual or ultrasounds checking, for example.

When a blade has being inspected, the platform is lowered and then the wind turbine is rotated to place another of the blades in vertical position which is in turn inspected and the operation is repeated until all the blades have being checked.

A major difficulty of this type of non destructive testing method comes from the fact that the checking interventions are carried out by operators located on a platform which rises by need at several tens of meters above the ground level under difficult conditions which requires a long stopping period of the wind turbine to carry out the inspection, limit the quality of the checks and present potential risks for the operators whose the control is constraining.

Moreover such nacelles require themselves many safety checks to be used in the respect of the standards in force.

The document US 2010/0132137 presents another type of device which implements an autonomous robot that moves on the blade. In this case the blade to be checked is placed in a horizontal position with its leading edge directed to the top and the robot comprises rolling means bearing on the leading edge of the blade in order to move it along the span of the blade.

The capacities of this type of robot prove however to be limited by the fact that only regions close to the leading edge of the blade can be checked and by the fact that the position of the robot can be unstable.

Moreover, the displacement of the robot in contact with the blade requires to take precautions in order that the blade was not likely to be damaged during a nominal operation or not of the robot.

In addition, the visual checking techniques make it only possible to detect visible defects from the blade outside and of a sufficient size to be observed, i.e., more generally at a very advanced stage of the defect, and the ultrasonic inspection techniques which makes it possible to detect internal defects take a long time to be implemented.

The present invention simplifies the testing of wind turbine blades and improves the quality of their maintenance by making it possible to carry out quality checks at closer intervals without prolonged immobilization of the wind turbine in order to detect as soon as possible any damage on a blade.

For that, the NDT method of the invention, for non destructive testing of a wind turbine blade, in which the structure includes a skin that, at least partially, determines a blade external surface and a blade internal hollow volume, taking into account structural or not structural elements that may be located within the blade, includes:

a first step for loading the blade structure by a modification of at least one physical characteristic of a fluid, in particular, air if the blade internal volume is kept in relation to the atmosphere, filling out the blade internal hollow volume;

a second step for observing regions of the blade external surface to be checked, this observation including the carrying out of contactless measurements, by means of one or more sensors maintained remotely from the external surface, of at least one physical parameter, sensitive to the loading of the first step, on points of the blade external surface in order to establish a measured map of the physical parameter values measured for the regions to be checked;

a third step for detecting the anomalies by comparing values measured during the second step with expected nominal values for a blade without notable defect, i.e. corresponding to values of an operational blade.

In a first implementation of the NDT method, the mainly modified physical characteristic corresponds to the fluid temperature in the blade internal hollow volume. This fluid temperature is brought to a value different, higher or lower, from the temperature outside at the blade during the first step and the physical parameter measured during the second step corresponds to a temperature of the blade external surface.

The temperature change is obtained either by heating or by cooling the fluid by conventional heating or cooling means and by providing a circulation of the fluid within the blade hollow volume.

In this implementation mode a fast and accurate measurement is advantageously carried out by an infra-red thermography measurement without any physical contact using a measurement sensor which is, during the measurement, kept remotely from the blade external surface.

In another implementation of the NDT method, the physical characteristic mainly modified corresponds to a pressure of the fluid in the blade inner hollow volume.

This pressure of the fluid is brought to a value different from the pressure at the blade outside, either to a lower pressure, or to a higher pressure, during the first step and the physical parameter measured during the second step corresponds to a geometrical dimension of the blade external surface that characterizes the geometrical form of this external surface or to a dimension change corresponding to the deformation of this external surface under the effect of the pressure change.

According to this application of the method, the generation of a differential pressure is carried out by means of a pump tightly connected to the blade hollow volume which, at least during the check, is not directly connected to the surrounding air.

In this implementation mode, the geometrical dimensions of the blade external surface or of its deformations are advantageously measured without any contact by a telemetry laser method, a numerical photogrammetry method, an interferometry laser method or by a shearography method.

In an implementation mode, the anomaly detection carried out at the third step includes a step of comparison of the value measured at each point with measured values at points close to the considered point, in order to establish a contrasts map of the measured parameter values and includes a step of correlating said contrasts map with internal structures of the blade, which makes it possible to detect anomalies without it being necessary to use a comparison reference other than the values measured on the blade subjected to the checking.

In another implementation mode, the measured map is compared with a reference map of the measured parameter values which is advantageously a reference map established by measurement according to the first and second steps of the method on one, possibly on the blade subjected to control NDT and checked before its first use, or on several blades considered as being without defect, thus making it possible to carry out an average reference map representative of all the blades of the same model, or is a theoretical reference map established by digital simulation of the method on a blade digital model, making it possible to carry out a reference map free from any artifact related to manufacture problems or not detected defect on a measured blade and also allowing to simulate defects to have a representation of its importance according to the method, or is a reference map established by mixing measured values and simulation values.

In order to facilitate the interpretation of observable anomalies relatively to the reference map, the NDT method advantageously includes a fourth step for characterizing defects by comparing the characteristics of identified anomalies, in real time during measurement or in differed time, of each anomaly observed with known anomalies whose characteristics are stored in an anomaly data base.

The invention also relates to a NDT system for non destructive testing adapted to the implementation of the inventive NDT method intended to check the structural integrity of a wind turbine blade, including a skin determining a blade external surface and an blade internal hollow volume, which includes:

an aerothermic device for modifying the physical conditions of a fluid filling out the blade internal hollow volume;

a measurement device implementing one or more contactless sensors for at least a physical parameter of the blade external surface;

a measurement processing device configured to establish a measured value map of the at least one parameter on the blade external surface and to identify the anomalies of the measured value map.

According to a first realization form, the NDT system corresponding to the first implementation mode of the method, the aerothermic device is a heating device, for example including electric heating resistances, or a cooling device, for example, a refrigeration compressing group, modifying a fluid temperature in the blade internal hollow volume to bring this temperature to a value different from the blade external temperature, by positive value or negative value, and the contactless measurement device implements a thermal camera measuring the temperature of the blade external surface or any other sensor allowing to measure without any contact a value representative of the blade external surface temperature.

In a realization form, which makes it possible to have beforehand equipped blades for which the installation of the NDT system to carry out a checking is simplified, heating means of the heating device intended to modify the fluid temperature in the blade hollow volume are fixed into the hollow volume, inside the blade, these heating means including one or more electric heating resistances and/or means to keep the fluid in circulation into the hollow volume.

According to another realization form, the aerothermic device is a pressure generating device, for example, a gas pump, modifying a fluid pressure, for example, air, in the blade internal hollow volume and holding during the check operations this pressure at a controlled value different from an external pressure of the blade with a preset, positive or negative, difference.

For the needs of this realization form of the NDT system, the contactless measurement device in a first realization form implements one or more devices to measure the geometry of the blade external surface during the check by numerical photogrammetry or, in another realization form, implements a scanning telemeter to measure the geometry of the blade external surface during the check by telemetry.

Other contactless measurement device of the sensor such as a laser interferometer or a shearography device are also usable to measure the deformations of the blade external surface under the effect of the fluid pressure change within the blade.

These devices implemented in the NDT system present the advantage to be industrially available and relatively inexpensive what makes it possible to consider the possibility of installing an aerothermic device permanently into each wind turbine in order to facilitate the installation of the NDT system at the time to carry out the check operations.

The choice of a measurement device with a contactless sensor and of a sensor support making it possible to carry out a scanning of the blade takes advantageously into account the quickness and the precision of the required measurements and also the environmental conditions which can be very different according to the wind turbine implantation.

According to the wind turbine accessibility conditions and according to whether it is privileged the checking quickness or another condition, the contactless measurement device can during measurements be fixed remotely from the wind turbine, typically from about the height of the wind turbine, on the ground or on a terrestrial vehicle or on a surface vessel or be fixed to an airborne platform movable along the blade near said blade to take measurements at a reduced distance, typically of about the length of the blade aerodynamic profile chord, or also near to blade surface, carried by a robot moving on the blade and bearing on the blade.

The airborne platform is, for example, maintained in levitation by a drone or micro-drone with a rotary aerofoil, controlled in position relatively to the blade, or is maintained in levitation by a captive balloon lighter than the air, controlled in position relatively to the blade to be checked.

Figure 2A:
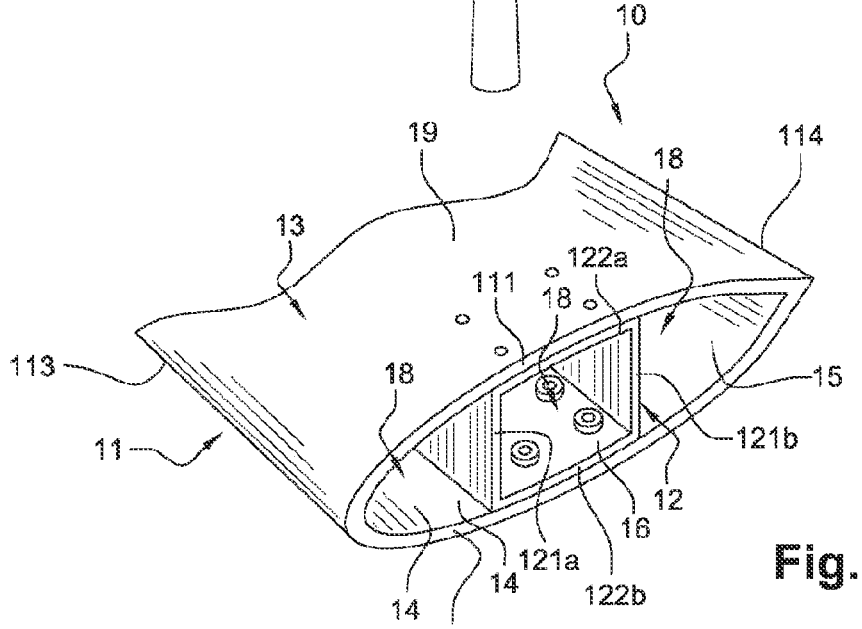
Figure 2B:
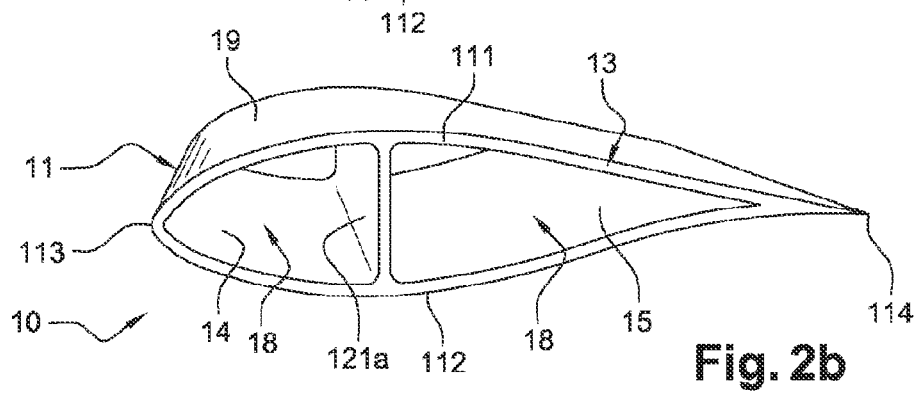
Figure 3:
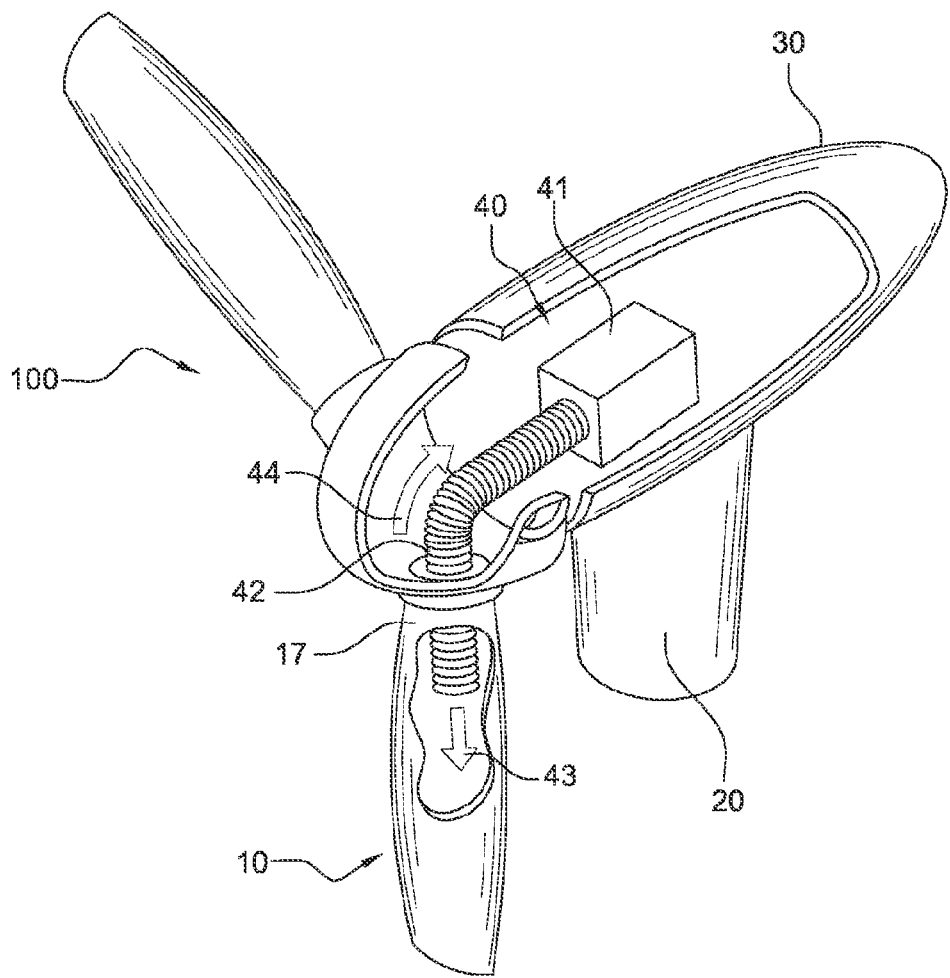
Figure 4A:
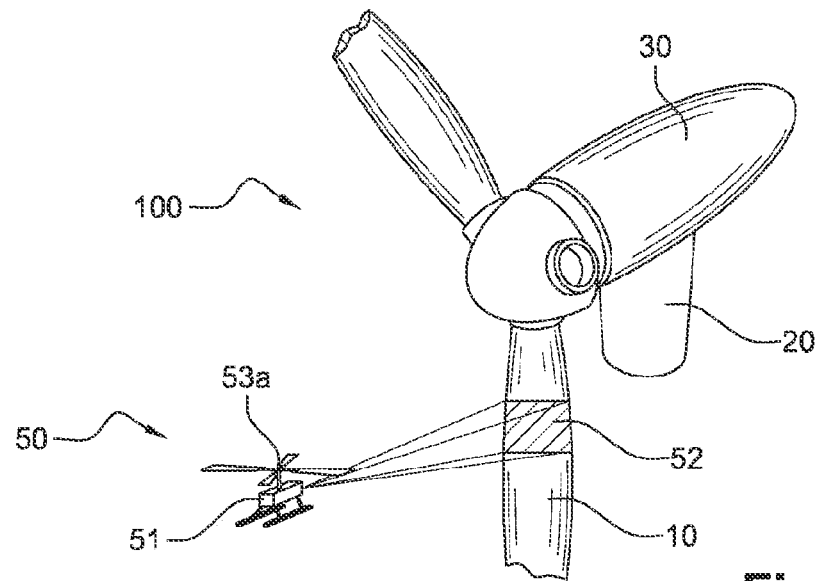
Figure 4B:
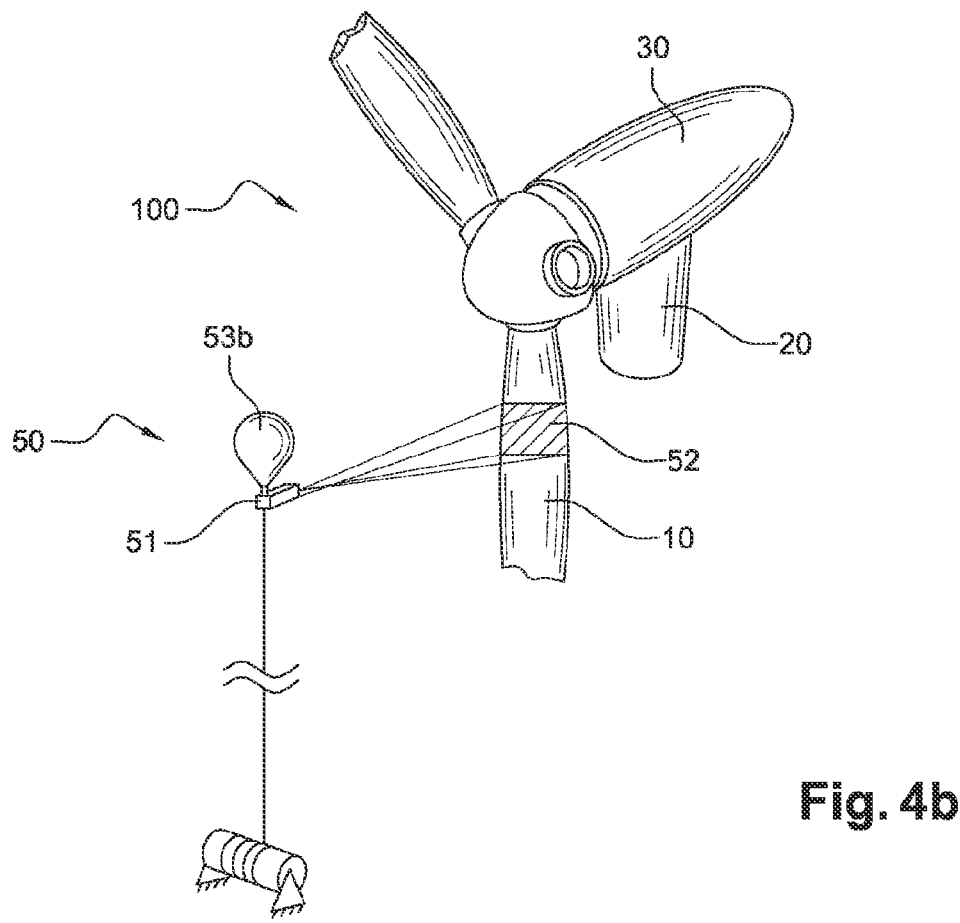

Other characteristics and advantages of the invention will be better understood at the reading of the following description of nonrestrictive examples of embodiment of the invention with reference to the drawings that represent:

FIG. 1: an overall perspective view of an example of large sized three-bladed wind turbine;

FIG. 2a: a perspective view of a blade section showing the internal structure of a blade comprising a box type member including two webs;

FIGS. 2b: a perspective view of a blade section showing the internal structure of a blade comprising a member including only one web separating a leading edge box from a trailing edge box;

FIG. 3: a diagrammatic example of an aerothermic device arrangement for the NDT system of the invention, FIG. 4a: an illustration of a first embodiment of an airborne platform for the measurement device of the inventive NDT system by means of a drone or micro-drone with a rotary aerofoil, FIG. 4b: an illustration of a second embodiment of an airborne platform for the measurement device of the inventive NDT system by means of a captive balloon.

Figure 5:
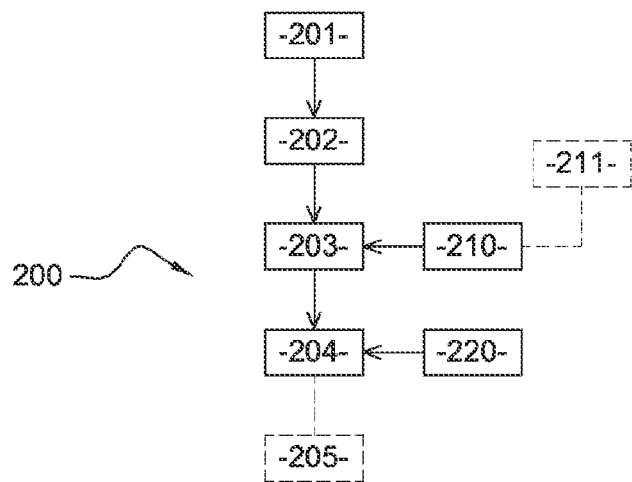

FIG. 5: a simplified synoptic presentation of the method of the invention. This method for non destructive testing, known as NDT, of a blade 10 on a wind turbine 100, as represented on FIG. 1, is based on the implementation of a transmission measurement technique with a remote observation of the blade, i.e., without any contact of measurement sensors.

In this document the expression "contactless measurement" means that a measurement is carried out without the sensor or sensors implemented to carry out the measurement being in physical contact with a blade surface to be checked, support systems for the sensor or sensors can however bear on the blade in order to keep the sensor or sensors remotely from the surface.

The wind turbine blade 10 is a lifting aerodynamic form of great extent whose external surface 19 is geometrically given by a succession of aerodynamic section 11 each corresponding to the geometry of an extrados covering 111 and an intrados covering 112 between a leading edge 113 and a trailing edge 114 and that determine the blade external surface 19, as illustrated on FIGS. 2a and 2b.

Blade 10 is fixed on a rotating shaft solidary with a technical nacelle 30 located in a higher part of a carrying post 20 and that gathers functional elements of the wind turbine: power generator, gear box, blades pitch control . . . not detailed here.

Blade 10, as generally most of the large-sized wind turbine blades, is hollow, for reasons of a maximum reduction of its mass and to save the matter from which it is made.

To provide its aerodynamic functions and the transmission of the aerodynamic forces generated during its operation, blade 10 is made in the form of a box type structure less or more complex but including generally, as illustrated on FIG. 2a, a longitudinal box forming an elongate member 12 of the blade along its span.

Such an elongate member 12 is, for example, of a substantially rectangular section, i.e. comprising at least two webs, a front web 121a and a rear web 121b, connected by soles 122a, 122b and is covered with a skin 13 giving to the blade its aerodynamic profiles, variable according to the position along the blade span.

Skin 13 can be made from several elements to reconstitute the intrados 112 and extrados 111 coverings of the blade as well as on its leading edge 113 than its trailing edge 114 sides that are assembled the one to the other and to the elongate member 12 according to known methods such as, for example, by added fixings and/or sticking.

According to this implementation of the blade 10, said blade has a blade hollow volume 18 internal to the skin 13 with a whole multi-boxes structure, in the case illustrated on FIG. 2a, a leading edge box 14 between the leading edge 113 and the front web 121a of the elongate member 12, a trailing edge box 15 between the rear web 121b of the elongate member 12 and the trailing edge 114 and a member box 16 between the front 121a and rear 121b webs of the elongate member.

It must be noted that the elongate member 12 can also include only one web 121 as illustrated on FIG. 2b, and in this case, the rigidity in torsion of the blade is ensured by the leading edge 14 and/or trailing edge 15 boxes in the absence of a member box, or on the contrary can include a member including more than two webs and delimiting a plurality of member boxes, a not represented solution.

The structural elements of the blade that are located in the volume determined by the external surface 19 are here partly or entirely gathered, according to the case, under the expression "internal structure".

According to the NDT method 200 of the invention, presented in a synoptic form on FIG. 5, the blade 10 undergoes a loading of its structure by a change on at least one physical characteristic of a fluid filling out the hollow volume 18 of the blade and the effects of this internal loading are observed on the blade external surface 19 by the measurement of at least one physical parameter, sensitive to the internal loading, on various points of said external surface in order to detect, by comparison to a reference value of the physical parameter at each point, anomalies on the measured parameter value that are likely to correspond to blade structure defects.

In a first implementation mode of the method 200, the loading of the structure is carried out by a change on the fluid temperature, a priori, air at the environmental pressure or, according to the case, any other fluid used to fill out the hollow volume 18 and used as coolant in this first mode, occupying the hollow volume 18 and the effects of this temperature change on the structure are observed from the outside of said blade by thermography means so that the consequences of the internal temperature change and the temperature gradient that results from it between the inside and the blade outside are observed by their thermal effects at the external surface 19 of skin 12, 13 to which the energy is propagated in the form of heat.

In a first step 201, the fluid temperature inside the blade is modified relatively to the air temperature at the blade outside.

This temperature change of the internal fluid, induces a heat flow into the structure between the blade inside and the blade outside that depends in each point on local characteristics of the structure crossed by this heat flow of which the effects can be observed on the blade 10 external surface from the blade outside where they result in temperature differences that are related to irregularities of the internal structure.

It must be noted that the temperature inside the blade can be brought to a value higher or a value lower than the outside temperature to induce the expected heat flow, the effects being then translated on the external surface 19 of the blade by sites more or less hot or points more or less cold according to the site of the blade surface considered relatively to the external ambient temperature according to whether the internal fluid temperature is increased or decreased.

In a second step 202, the blade external surface 19 is observed in order to establish a temperature map of said external surface, in the practice, a map of the temperatures measured in various points of regions of the blade external surface subjected to the check where each measured point of surface is associated to the measured temperature.

In a third step 203 the map of the measured temperatures established during the second step 202 is analyzed to identify thermal anomalies, i.e. temperature differences on the blade surface that do not correspond to the temperature differences expected on the blade surface.

The identification of the thermal anomalies includes, in an embodiment of this third step 203, a step of identification of thermal contrasts on the temperature map which do not correspond to effects expected by the presence of internal structure elements, more particularly that does not correspond to the thermal contrasts expected due to the presence of the internal structure when the observed region corresponds to the known presence of such structure elements inside the blade.

The thermal anomalies are, in particular, identified by the sign of a difference between the measured temperature and the expected temperature, and/or by a contrast relating to the intensity between the thermal anomaly, i.e. an absolute value of a difference between the measured temperature and the expected temperature, and/or by an extent of the region having a thermal anomaly.

In a method for implementing this third step, the thermal anomalies are detected by an analysis of contrasts of the temperature map resulting from measurement, i.e., that each point of the blade surface for which the temperature is measured is compared to measured temperatures of points close in order to identify temperature gradients on the blade surface that do not correspond to characteristics of internal structure elements.

In another method for implementing this third step, the map of the measured temperatures, eventually translated into a map of the thermal contrasts, i.e. related to a reference temperature in order to neutralize the influence of the outside temperature during the measurement, is compared to a temperatures or a thermal contrasts reference map, called a reference map, beforehand obtained 210 on an operational blade of a similar structure, in order to extract a map of the thermal anomalies corresponding in any measurement point to the difference of temperature or thermal contrast intensity between these two maps.

It is here advisable to note that a blade comprises many normal structure "accidents", as a consequences of its internal structure and of the blade manufacturing processes that lead to a complex reference map on which effects of minor structure defects are not easily directly observable.

The reference map is, for example, obtained 210 by tests carried out, a priori, at the factory, on one or preferably several operational checked blades, if necessary by tests 211 on the blade subjected to check in use, by any adapted NDT method, for example by ultrasounds in order to establish a reference map established by the measurement.

Another method to carry out the reference map consists in carrying out a detailed digital model of the blade structure and to determine by digital simulation one or more reference maps established in a theoretical way.

In a fourth step 204, the map of the thermal anomalies is analyzed to identify the type and the importance of the defects corresponding to these thermal anomalies.

The type and the importance of a defect are, in practice, given according to the extent of the thermal anomaly observed, of the site of the anomaly, in particular according to the importance of the underlying internal structure, and the intensity of the thermal anomaly.

By way of nonrestrictive examples, a thermal anomaly corresponding to an increased thermal contrast relatively to the expected contrast, of the same sign than the temperature difference between the fluid within the blade and the blade outside, and delimited by a narrow and lengthened region correspond, with a high probability, to a crack into a wall, and a diffuse and wide thermal anomaly having a thermal contrast whose evolution is of a reversed sign relatively to the temperature difference between the fluid inside the blade and the blade outside correspond, with a high probability, to a region of local delamination of the blade skin 13 or an unsticking of internal structure elements.

Advantageously a data base 220 showing the anomalies characteristics likely to be observed makes it possible to more quickly characterize the defects.

Such a data base 220 is advantageously carried out by digital defects simulation on a digital blade model in order to characterize at least the defects considered as the most critical during an safety analysis of the wind turbine.

Preferably, this data base 220 is enriched according to the carried out observations which highlight, during the life of the wind turbines that can exceed 15 years, defects having been detected by the method of the invention then characterized within the framework of the blades maintenance.

Once a defect is detected and characterized, conventionally, the adapted maintenance actions 205 are carried out: reinforced monitoring of the defect and its evolution, repair on site or blade dismounting for repair.

An advantage of the method is that it makes it possible to carry out early and precise defects detections and thus to reduce the costs of monitoring and maintenance and to decrease the risks of unavailability of the wind turbine.

In another implementation mode of the method, the loading 201 of the blade structure is carried out by the application of a positive or negative differential pressure between the fluid occupying the blade hollow volume 18 and the air at the outside of the blade.

In this implementation mode, the differential pressure, limited to values compatible with the blade structure strength, causes structural deformations of the blade observable at the external surface 19 by methods intended to measure the geometrical shapes of an object.

To take contactless measurement of the geometrical form of the blade external surface 19, it is, for example, implemented a measurement method by laser telemetry or numerical photogrammetry or laser interferometry or also by shearography.

Similarly to the described first implementation mode, a map of the external surface 19, here a map of the geometrical deformations of said surface under the effect of the differential pressure is carried out 202 and then analyzed 203 in order to identify the geometrical anomalies of the blade 10 undergoing the differential pressure, i.e. the deformations of the external surface 19 which do not correspond to expected geometrical deformations, taking into account the internal structure.

The identification of the geometrical anomalies results in an embodiment of the third step 203 from the identification of deformations which, relatively to regions near the blade surface do not correspond to elements of the internal structure due to the positions of the deformations on the blade surface and/or to their forms and/or to their amplitudes.

In another embodiment, the anomalies map is obtained by carrying out a subtraction between the geometry of the external surface 19 of the blade 10 during the check while undergoing the differential pressure and the geometry of the external surface of a similar blade, considered as operational also undergoing a differential pressure, this last geometry of the external surface 19 corresponding to a reference map in this case of the geometrical forms obtained with the differential pressure, eventually corrected from the effects of differences between the pressures applied between the two tests.

Thus the anomalies map presents the regions of the blade whose deformations are not expected with information on the position of said regions and the amplitude of said deformations.

The shape of the operational blade undergoing a differential pressure and being used as reference to the determination of anomalies can be obtained 210 by digital simulations or physical tests on blades beforehand checked and considered as being operational, if necessary obtained 211 by physical tests on the blade subjected to the check in use.

The anomalies are then compared 220 with a defects data base giving the characteristics of known anomalies, the characteristics being established by simulation or experiment.

The invention also relates to a NDT system for the non destructive testing of a wind turbine blade according to the NDT method of the invention.

For the implementation of the first described mode of the NDT method, the NDT system includes a first aerothermic device 40 for modifying the fluid temperature within the blade 10, as illustrated on FIG. 3.

The aerothermic device 40 includes a generator 41 which modifies the fluid temperature, being advantageously air, and generates in this example an internal air 43 at a temperature different from the external air, hotter or colder than the air external from the blade 10.

The temperature difference is, on the one hand, sufficient to cause thermal gradients into the structure of the blade 10 leading to temperature variations detectable on the blade external surface 19 and, on the other hand, limited to temperature values compatible with the materials and the assembly processes implemented on the blade.

In an example of realization implementing an overheated fluid sent inside the blade, the fluid temperature for example lies between 70 degrees centigrade and 120 degrees centigrade, this temperature being acceptable according to these two criteria taking into account the conventional means for detecting the temperature variations likely to be implemented and the present technologies of the wind turbines blades.

Although the smallest dimensions of the detectable defects depend theoretically on the minimal value of the temperature differences measurable by the implemented means, it is advantageous to consider detectable temperature differences on the blade surface of about 0.01° C. in order to avoid the use of complex and expensive measurement means whose implementation in the wind turbine environment would be too much penalizing economically. A thermal camera compatible with the detection of temperature differences of this amount is able, with an adapted optics, to provide a resolution better than the centimeter at a distance of ten meters.

In a preferred implementation mode the air generator 41 is installed in the technical nacelle 30 where it is securely fitted and dedicated to the considered wind turbine in order to allow checking operations without requiring particular logistics to handle said generator.

The aerothermic device 40 also comprises a distributor 42 for the air produced by the air generator 41.

Such a distributor 42 consists mainly in one or more flexible or rigid injection piping that canalize the hot or cold air of the air generator 41 inwards the blade 10 at a blade bottom 17 so that the hot or cold air is injected into the blade hollow volume 18 by an axial opening of said blade bottom.

In this case, it is taken advantage of the general structure of wind turbine blades of which the blade bottom 17, corresponding to the end located on the side fixed to the nacelle 30, is accessible.

Into the case of the invention, the air 43 is injected into hollow volume 18 of blade 10 in order to follow a predetermined circuit such as the whole of the blade hollow volume, or at least the desired volumes, are crossed by a continuous flow of the heat or cold air 43 coming from the air generator 41.

To guarantee such a result, it is advantageously used the blade internal structure 10, if necessary adapted so that the air 43 injected by the blade bottom 17 cross all the blade along its span up to the proximity of the blade end, opposed along the blade span to the blade bottom, by at least one of the boxes 14, 15, 16 and follows an opposite path from the end towards the blade bottom by the other boxes.

In the example of blade whose section is illustrated on FIG. 2a, air is for example injected into the member box 16 and follows an opposite path trough the leading edge box 14 and trailing edge box 15 formed by the skin of the blade.

The webs 121a, 121b of the elongate member include openings which allow the air to circulate from the box into which the air is injected towards the boxes by which the air follows an opposite path.

These openings are arranged near the blade end and can be distributed along the span to distribute the injected air at various points of the other boxes and to ensure a fast and homogeneous temperature setting of the fluid into the hollow volume 18.

To ensure the air circulation, the injected air 43 leaves 44 also the blade at the blade bottom 17.

The air 44 leaving the blade can be released outwards while circulating around the injection piping, but advantageously the air is held in closed loop in order to assure a better heating or cooling effectiveness and the air 44 leaving the blade is returned towards the air generator 41 to be recirculated therein. In this case the leaving air can be released in nacelle 30 where it is taken by the air generator 41 or return from the blade bottom 17 towards the air generator 41 by means of one or more dedicated output piping, a not represented solution.

The fitting of injection and output piping does not present a particular problem but, taking into account the rotation of the wind turbine blades in operation, the piping is preferably dismountable to avoid complex rotary joints.

In an advantageous way, the blades 10 of the wind turbine 100 are checked one after the other and the dismountable piping make it possible to successively connect the air generator 41 to each blade in order to carry out the checks.

In an alternative of realization, heating means such as one or more electric resistances are installed, permanently or during a check, inside the blade in order to heat the air within the blade, air which is advantageously forcedly circulated within the blade by one or more ventilators or turbines, themselves also permanently installed or not inside the blade.

For the implementation of the first described mode of the method, the system also comprises a second device 50 for measuring the temperature of the blade outside surface.

The measurement device 50 carries out a temperature map of the blade 10 on each one of these faces, at least in regions of the blade 10 having to be subjected to a check by the method.

In a preferred embodiment, the second device is a thermography system implementing a contactless sensor 51 such as a thermal camera.

The thermal camera itself a thermal camera of a conventional model implementing an infra-red sensor and whose performances as for temperature detection than resolution are selected according to the precision requested for the defects detection.

Sensor 51 is carried by a support which makes it possible the field of a camera objective to sweep all the blade external surface to be checked.

Such a support is for example a terrestrial support, i.e. bearing on the ground or on a terrestrial vehicle or on a surface vessel, in the case of wind turbines established in the marine environment, during the measurement, such as an articulated support carrying the sensor 51 to take measurements on the various regions of the blade external surface.

The movement of the support, if necessary stabilized, can be manual or automatic and advantageously the contactless measurement device includes localization means intended to associate each measurement to the measured region of the blade surface.

Such localization means can comprise one or more position encoders indicating the support position and orientation, corresponding, in practice, to a region 52 of the blade surface being measured by the sensor so that each image carried out by the sensor can be associated to the part of the blade 10 surface to which it corresponds.

Such localization means can also include identification means carried by the wind turbine blade, for example a graduated scale along the span on the blade external surface (19) which is read or recorded simultaneously with the measurements taken by the sensor (51).

In another implementation mode, the support is an airborne platform maintained in levitation by a flying device such as a drone or a micro-drone with a rotary aerofoil 53a, as illustrated on FIG. 4a, or also such as a captive balloon 53b inflated by means of a gas lighter than the air, as illustrated on FIG. 4b, which carries the sensor 51 and which is moved along the blade 10 at a selected distance from the blade surface.

In these examples of realization the piloting of the airborne platform 53a, 53b can be carried out by an operator from the ground or by automatic piloting.

In this implementation mode, advantageously position encoders of the airborne platform in the space, for example by laser telemetry, and if necessary for orientation of the sensor 51 on said airborne platform, and/or by the detection of reference marks such as visible targets on blade external surface (19), make it possible to pilot the airborne platform and to associate each image carried out by the sensor at the surface part 52 of the corresponding blade.

The use of an airborne platform 53a, 53b makes it possible to realize, with inexpensive sensors, close measurements of higher resolution and precision than when the images are taken remotely.

In another not illustrated implementation mode of the support, a robot is movably assembled on the blade 10 in order to be able to move along all the span undergoing the check of said blade by bearing on the blade itself. The robot is carrying at least a contactless sensor, advantageously a plurality of sensors taking measurements on different parts of the blade external surface, for example the intrados and/or the extrados and the region of the leading edge, in order to carry out measurements on a wide blade surface in only one course along the span or a direct and return trip along the span.

According to the implementation mode of the support for one or more sensors, said sensors are fitted to the distances from the blade surface 10 to which the measurements must be taken. For example in the case of a sensor of the camera type, the camera will be equipped with an objective having a more or less long focal distance according to whether the observation is carried out remotely from the ground or from an airborne platform with an objective with a narrow field or from a robot, necessarily at a close distance with an objective having a broad field.

For the implementation of the second mode described of the method, the first aerothermic device 40 is a pressure generator tightly connected by the distributor 42 to the internal hollow volume 18 of the blade 10 in order to bring the fluid, for example, air, into this internal volume to a pressure higher or lower than the external air pressure by maintaining the difference of the pressures, or the differential pressure, to a desired preset value substantially constant.

In this case, the various boxes 14, 15, 16 of the blade communicate to each other by via openings on the webs 121a, 121b of the elongate member to make it possible for the pressure to be uniform inside the blade.

The differential pressure having to be maintained between the interior and the exterior of the blade during the measurements is a function of the blade structure and of the sensitivity of the means intended to measure the deformations of the blade external surface.

In the practice, for the known blades, a differential pressure from 10 to 100 millibar is generally sufficient to produce measurable deformations without any risk to damage the blade undergoing this differential pressure.

In this embodiment, the second measurement device 50 takes geometrical measurements of blade outside surface by means of a contactless sensor 51 reproducing the geometry of the surface region 52 observed by said sensor.

Such a sensor 51, for example, consist in a scanning laser telemeter, which makes it possible to obtain a measuring accuracy of about 0.01 mm, or in a numerical photogrammetry device, or in a laser interferometer or in a shearography device, devices which make it possible to obtain close accuracies, which, as in the described first embodiment, can be placed on the ground, fixed to an airborne platform 53a, 53b or carried by a robot intended to move along the blade according to the required accuracy and the performances of the used sensors.

In addition, the NDT system also comprises a measurement processing device.

Such a measurement processing device comprises advantageously a calculator with calculating units, memories and numerical data storage means in order to receive, in real time or differed time, the measurements carried out, to store the reference maps and the anomaly data bases and display means to present the results to an operator responsible of the checking.

The calculating units are programmed to build the measured value map representative of the measured parameter on the blade surface and to display the obtained maps and, preferably, to build and display the anomaly maps which are, for example, displayed on a screen and/or printed by visualizing the anomalies on a graphical representation of the blade by means of a color code representing the intensity of the anomaly on each considered point of the blade.

The invention claimed is:

1. A NDT method (200) for non destructive testing of a wind turbine blade (10) attached to a wind turbine (100), a structure of said blade including a skin (13) determining a blade external surface (19) and a hollow volume (18) at the interior of the blade, said NDT method including:
    a first step (201) for loading the blade structure, fixed to a turning shaft attached to a technical nacelle (30) located in an upper part of a carrying post (20), by a modification of at least one physical characteristic of a fluid filling out the blade hollow volume (18), using an aerothermic device (40) installed in the wind turbine;
    a second step (202) for observing regions of the external surface (19) to be checked, said observation comprising the carrying out of contactless measurement with a measurement sensor, fixed remotely from the wind turbine, of at least one physical parameter, sensitive to the loading of the first step (201), on points of the external surface (19) in order to establish a measured map of the physical parameter values measured for said regions to be checked; and
    a third step (203) for detecting structural anomalies in the blade by comparing values measured during the second step with expected values for a blade without any notable defect.

2. The NDT method according to claim 1, wherein the at least one modified physical characteristic corresponds to the fluid temperature into the hollow volume (18), said temperature of said fluid being brought to a value different from the temperature at the blade outside during the first step (201), and wherein the physical parameter measured during the second step (202) corresponds to a temperature of the blade external surface (19).

3. The NDT method according to claim 2, wherein the temperature of the blade external surface (19) is measured in a contactless manner by infra-red thermography.

4. The NDT method according to claim 1, wherein the at least one modified physical characteristic corresponds to a fluid pressure into the hollow volume (18), said pressure of said fluid being brought to a value different from the pressure at the blade outside during the first step (201), and wherein the physical parameter measured during the second step (202) corresponds to a geometrical dimension of the external surface (19) characterizing the geometrical form of said external surface.

5. The NDT method according to claim 4, wherein the geometrical dimension of the external surface (19) is measured by one of the laser telemetry, numerical photogrammetry, laser interferometry or shearography methods.

6. The NDT method according to claim 1, wherein the detection of anomalies carried out in the third step (203) includes a step for comparing the measured value at each point with measured values at points near to the considered point in order to establish a map of value contrasts of the measured parameter and includes a step for correlating said contrasts map with internal structures of the blade (10).

7. The NDT method according to claim 1, wherein the detection of anomalies carried out in the third step (203) includes a step for comparing the measured map with a reference map, said reference map being a reference map of the measured parameter values established by measurements according to the first and second steps (201, 202) of the method, on one or more blades considered as without defect, or a reference map established by a digital simulation of the method on a digital blade model, or it is an hybrid map obtained by hybridization of all or a part of reference maps established by measurement or digital simulation.

8. The NDT method according to claim 1, comprising a fourth step (204) for characterizing defects by a comparison of the anomalies identified at the third step (203), in real time during the measurement or in differed time, of each anomaly observed with known anomalies whose characteristics are stored in a bank of anomaly data.

9. A set including a wind turbine (100) and a NDT system for non destructive testing intended to check the structural integrity of a wind turbine blade (10), fixed to a turning shaft attached to a technical nacelle (30) located in an upper part of a carrying post (20) of the wind turbine (100) according to the process of claim 1, said blade comprising a skin (13) determining a blade external surface (19) and a blade hollow volume (18), comprising:
    an aerothermic device (40) intended to modify physical conditions of a fluid filling out the blade internal hollow volume (18) and implemented either in the technical nacelle (30) or the wind turbine blade (10);
    a contactless measurement device fixed remotely from the blade to be checked during the measurements and implementing at least a contactless sensor (51) of at least a physical parameter of the blade external surface (19);
    a measurement processing device configured to establish a measured value map of the at least one parameter on the blade external surface (19) and to identify anomalies of said measured values map,
    wherein the aerothermic device (40) is a heating or cooling device intended to modify the fluid temperature within the blade hollow volume (18) at a value different from the temperature at the blade outside,
    wherein the measurement device provided with at least a contactless sensor (51) implements a thermal camera measuring the temperature of the blade external surface (19), and
    wherein the contactless measurement device (50) is fixed on the ground, or on a terrestrial vehicle, or on a surface vessel, remotely from the wind turbine during the measurements.

10. A set including a wind turbine (100) and a NDT system for non destructive testing intended to check the structural integrity of a wind turbine blade (10), fixed to a turning shaft attached to a technical nacelle (30) located in an upper part of a carrying post (20) of the wind turbine (100) according to the process of claim 1, said blade comprising a skin (13) determining a blade external surface (19) and a blade hollow volume (18), characterized in that it comprises:
- an aerothermic device (40) intended to modify physical conditions of a fluid filling out the blade internal hollow volume (18) and implemented either in the technical nacelle (30) or the wind turbine blade (10);
- a measurement device implementing at least a contactless sensor (51) of at least a physical parameter of the blade external surface (19); and
- a measurement processing device configured to establish a measured value map of the at least one parameter on the blade external surface (19) and to identify anomalies of said measured values map,
- wherein the aerothermic device (40) is a heating or cooling device intended to modify the fluid temperature within the blade hollow volume (18) at a value different from the temperature at the blade outside,
- wherein the measurement device provided with contactless sensors (51) implements a thermal camera measuring the temperature of the blade external surface (19), and
- wherein the contactless measurement device (50) is fixed to an airborne platform (50) movable along the blade (10), near said blade.

11. The set including the wind turbine (100) and the NDT system according to claim 10, wherein the airborne platform (50) is maintained in levitation by a drone or micro-drone with a rotary aerofoil (53a) and controlled in position relatively to the blade (10) to be checked.

12. The set including the wind turbine (100) and the NDT system according to claim 10 wherein the airborne platform (50) is maintained in levitation by a captive balloon (53b) lighter than the air and controlled in position relatively to the blade (10) to be checked.

13. A set including a wind turbine (100) and a NDT system for non destructive testing intended to check the structural integrity of a wind turbine blade (10), fixed to a turning shaft attached to a technical nacelle (30) located in an upper part of a carrying post (20) of the wind turbine (100) according to the process of claim 1, said blade comprising a skin (13) determining a blade external surface (19) and a blade hollow volume (18), comprising:
- an aerothermic device (40) intended to modify physical conditions of a fluid filling out the blade internal hollow volume (18) and implemented either in the technical nacelle (30) or the wind turbine blade (10);
- a contactless measurement device fixed remotely from the blade to be checked during the measurements and implementing at least a contactless sensor (51) of at least a physical parameter of the blade external surface (19);
- a measurement processing device configured to establish a measured value map of the at least one parameter on the blade external surface (19) and to identify anomalies of said measured values map,
- wherein the aerothermic device (40) is a heating or cooling device intended to modify the fluid temperature within the blade hollow volume (18) at a value different from the temperature at the blade outside,
- wherein the measurement device provided with contactless sensors (51) implements a thermal camera measuring the temperature of the blade external surface (19), and
- wherein the contactless measurement device (50) is fixed on a robot movable along the blade (10) and bearing on said blade.

14. A set including a wind turbine (100) and a NDT system for non destructive testing intended to check the structural integrity of a wind turbine blade (10), fixed to a turning shaft attached to a technical nacelle 25 (30) located in an upper part of a carrying post (20) of the wind turbine (100) according to the process of claim 1, said blade comprising a skin (13) determining a blade external surface (19) and a blade hollow volume (18), comprising:
- an aerothermic device (40) intended to modify physical conditions of a fluid filling out the blade internal hollow volume (18) and implemented either in the technical nacelle (30) or the wind turbine blade (10);
- a contactless measurement device fixed remotely from the blade to be checked during the measurements and implementing at least a contactless sensor (51) of at least a physical parameter of the blade external surface (19);
- a measurement processing device configured to establish a measured value map of the at least one parameter on the blade external surface (19) and to identify anomalies of said measured values map; wherein the aerothermic device (40) is a heating or cooling device intended to modify the fluid temperature within the blade hollow volume (18) at a value different from the temperature at the blade outside,
- wherein the measurement device provided with contactless sensors (51) implements a thermal camera measuring the temperature of the blade external surface (19), and wherein the contactless measurement device is movable along the blade (10) and the contactless sensor (51) is free of any physical contact with the blade (10).

* * * * *